United States Patent
Cowan et al.

(10) Patent No.: US 6,466,911 B1
(45) Date of Patent: Oct. 15, 2002

(54) ELECTROTACTILE VOCODER USING HANDSET WITH STIMULATING ELECTRODES

(75) Inventors: Robert S C. Cowan, Prahan; Karyn L. Galvin, Elwood; Bich D. Lu, Altona; Rodney E. Millard, Eltham, all of (AU)

(73) Assignee: The University of Melbourne, Victoria (AU)

(*) Notice: Subject to any disclaimer, the term of this patent is extended or adjusted under 35 U.S.C. 154(b) by 0 days.

(21) Appl. No.: 09/424,771

(22) PCT Filed: May 29, 1998

(86) PCT No.: PCT/AU98/00404

§ 371 (c)(1), (2), (4) Date: Feb. 2, 2000

(87) PCT Pub. No.: WO98/53776

PCT Pub. Date: Dec. 3, 1998

(30) Foreign Application Priority Data

May 30, 1997 (AU) ............................................. PO 7091

(51) Int. Cl.⁷ ......................... G10L 21/06; A61F 11/04; A61N 1/36
(52) U.S. Cl. ...................... 704/271; 340/407.1; 607/56
(58) Field of Search ...................... 704/271; 340/407.1; 607/56

(56) References Cited

U.S. PATENT DOCUMENTS

| | | | |
|---|---|---|---|
| 3,831,296 A | 8/1974 | Hagle | |
| 4,390,756 A * | 6/1983 | Hoffmann et al. | 607/56 |
| 4,581,491 A * | 4/1986 | Boothroyd | 607/118 |
| 4,982,432 A | 1/1991 | Clark et al. | |
| 5,035,242 A | 7/1991 | Franklin et al. | |
| 5,047,952 A * | 9/1991 | Kramer et al. | 704/271 |
| 6,230,135 B1 * | 5/2001 | Ramsay et al. | 704/271 |

FOREIGN PATENT DOCUMENTS

| | | |
|---|---|---|
| EP | 0 054 418 | 6/1982 |
| GB | 2 133 697 | 8/1984 |
| WO | WO 91/03913 | 3/1991 |

* cited by examiner

Primary Examiner—Tālivaldis Ivars Šmits
(74) Attorney, Agent, or Firm—Nixon & Vanderhye (57) ABSTRACT

An electrotactile vocoder includes a handset (3) carrying stimulating electrodes (9) positioned adjacent openings (8) in the handset and electrically contacting the fingers when the handset is worn to cause stimulation of the digital nerves of the fingers, a speech processor/stimulator unit (2) for producing electrical stimuli at the electrodes (9) based on incoming speech and other information received by a microphone (1), the stimulator unit including circuit means for applying stimulating currents to the electrodes (9), the speech processor unit including means for encoding the presence of unvoiced speech components or for encoding information to a first formant F1 in addition to information relating to a second formant F2 and for applying the stimulating currents to selected pairs of electrodes.

14 Claims, 9 Drawing Sheets

ELECTROTACTILE VOCODER USING HANDSET WITH STIMULATING ELECTRODES

FIELD OF THE INVENTION

This invention relates to improvements in electrotactile vocoders.

BACKGROUND OF THE INVENTION

Hearing impairment limits access to speech cues and other acoustic information. The degree and ability of patients to use any residual hearing will determine how much the hearing-impaired person is able to understand using hearing aids. Most people with a significant hearing loss will need to use lip-reading to gain further speech information. Some cues to speech, such as place of consonant articulation, are relatively visible, however other speech cues, such as the formants of back vowels, and in particular consonant voicing, cannot be distinguished using visual cues. The role of tactile devices is to provide supplementary information which the hearing-impaired person can add to the visual and auditory information they receive. Tactile devices do not function as a complete speech information channel, and the wearer must continue to use visual and any available auditory information to maximise speech understanding.

Tactile devices provide speech information through electrotactile or vibrotactile stimulation of the tactile sense. Electrotactile devices use electrodes and low level electric current to stimulate the nerves endings of the tactile sense. Vibrotactile devices use vibrators to stimulate the tactile sense. Two different types of approaches may be employed to present speech information via tactile devices. The speech processing approach involves the tactile device selecting from the speech input certain aspects of the speech which are considered to be important for understanding the message. Alternatively, the bandpass approach involves filtering the entire speech input into a number of bands which are defined by frequency boundaries.

Many different body sites have been employed for use with tactile devices, some of the most common are the forearm, wrist, stomach, sternum and fingers. The transducers are usually held firmly against the skin—using elastic straps or a type of handset. See for example U.S. Pat. No. 4,982,432 (Clark et al) and U.S. Pat. No. 5,035,242 (Franklin et al). In general the user must also wear a microphone and a box which contains the speech processor or filter for the speech input, the stimulator circuitry and the power supply.

In our U.S. Pat. No. 4,982,432, in particular, the entire contents of which are incorporated herein by cross-reference, we have disclosed an electrotactile vocoder which has been found to assist severely and profoundly deaf adults, as well as providing assistance to speech perception and to articulation when used as a self-feedback device. Information provided through the tactile sense can be used directly, or combined with information provided through other sense modalities, such as vision (speech reading) or audition (hearing aids).

Trials of the electrotactile vocoder described in the above United States patent have been undertaken, and these trials have clearly established that the device can provide assistance to speech perception, and to articulation to persons having hearing impairment.

The electrotactile vocoder described in the above US patent comprises two main component elements:

(i) a handset and associated cabling, which incorporate eight electrodes positioned over the digital nerve bundles on each side of the four fingers of one hand, the purpose of which is to transmit the electrically-encoded speech information to the user; and (ii) a speech processor/stimulator unit and associated input microphone and cabling; the purpose of which is to detect incoming speech information, analyse and process this information, extract certain specific speech feature components as directed by the speech processing program implemented, electrically encode this information as changes in the stimulus electrical parameters of electrode selected, stimulus pulse width, and stimulus pulse rate, and send the electrical stimulus to the electrode handset for delivery to the user.

The trials referred to above have established that the electrotactile vocoder described in the above United States patent needed improvement in the following areas:

(i) the design of the electrotactile handset through which information is transmitted to the user and particularly the use of a large return electrode at the wrist;

(ii) the design of the speech processing strategy which is used to encode speech information for the user;

(iii) the circuitry and method of providing the electrical stimulus to the user, including the need for a large return electrode at the wrist, and for programming of the speech processor.

SUMMARY OF THE INVENTION AND OBJECT

It is the object of the present invention to provide improvements in electrotactile vocoders of the type described in the above US patent to thereby improve the ability of the electrotactile vocoder to provide benefit to hearing-impaired persons.

In a first aspect, the invention provides an electrotactile vocoder including a handset carrying stimulating electrodes which are positioned by the handset when worn to be in electrical contact with the fingers to facilitate stimulation of the digital nerves of the user, a speech processor/stimulator unit for producing electrical stimulus at the electrodes based on incoming speech and other information, said stimulator including circuit means for applying stimulating current to said electrodes and for switching at least selected ones of said electrodes to a non-active state when stimulating current is applied to any one of the other electrodes, and means for utilising the electrodes in said non-active state as ground or return electrodes.

By adopting the above strategy, the wrist electrode described in the United States patent referred to above is no longer required thereby substantially increasing the ease of use of the device, including the ability to provide an essentially one-piece handset which may be conveniently used by the hearing-impaired person and overcoming the electrophysiological problem of dielectric breakdown at the wrist electrode, which causes unpleasant levels of stimulation at the large return electrode under specified conditions, including dry climates.

In a preferred form, all electrodes which are in said non-active state are utilised as ground or return electrodes.

In another aspect, the invention provides an electrode handset for an electrotactile vocoder, including a body, four finger members extending outwardly from said body, each finger member having a shaped opening for receiving a finger and defining a ring-like member encircling the finger while leaving the fingers substantially free, opposed pairs of electrodes positioned adjacent each opening so as to make electrical contact with opposite sides of each finger in the region of the digital nerve when the fingers are inserted into the finger openings of the finger members, said ring-like members holding said electrodes in electrical contact with said fingers while allowing flexing of the hand or fingers without substantially affecting said electrical contact, said body also including an opening defining a wrist engaging strap for holding the handset on a hand with said electrodes engaging said fingers.

The body is most conveniently made of a resilient material, such as neoprene, and conductive wires extend from the electrodes to an electrical connector adapted for connection to the speech processor/stimulator of an electro-tactile vocoder.

The wires are preferably mounted on the surface of the electrode handset body and may be retained in position by an adhesive overlay or any other suitable means. In this way, the wiring is integrated into the body of the handset thereby reducing the likelihood of dielectric breakdown while ensuring a pleasant and effective stimulus delivered through the electrodes.

The speech processor/stimulator unit also incorporates a speech processing strategy which modifies the strategy utilised in the case of the electrotactile vocoder described in the above US Patent. In that strategy which was based on the multichannel cochlear implant developed by The University of Melbourne and Cochlear Limited and available commercially from Cochlear Limited, specific speech features (second formant frequency, second formant amplitude, and fundamental frequency) were electrically encoded and provided to the user through a specific pattern of stimulation of single electrodes. Following significant psychophysical and speech research, a new strategy, designated the UF2 strategy, has been developed which incorporates several novel features not anticipated from the earlier research and testing nor evident in published literature on tactile psychophysics. The specific encoding of an "unvoiced" stimulus is a novel approach which has not been employed in other devices. While other tactile devices have presented signals to the voiced/unvoiced context, they have all approached this problem by providing a signal to a "voiced" consonant. This approach has been ineffective, since both vowels and some consonants are voiced, and users have in general been unable to detect the difference between an unvoiced/voiced consonant at the start of a word immediately followed by a voiced vowel.

Thus, in another aspect, the invention provides an electrotactile vocoder including a handset carrying stimulating electrodes which are positioned by the handset when worn to be in electrical contact with the fingers to facilitate stimulation of the digital nerves of the user, a speech processor/stimulator unit for producing electrical stimulus at the electrodes based on incoming speech and other information, said stimulator unit including circuit means for applying stimulating currents to said electrodes, said stimulator unit including means for encoding the presence of unvoiced speech components, or for encoding information relating to a first formant $F_1$, in addition to information relating to a second formant $F_2$, and for applying stimulating currents to selected pairs of electrodes.

Thus, the new speech processing strategy includes the use of a "paired" rather than "single" dimension (ie. multiple-electrode sequential stimulation) to provide additional information. The use of this dimension was based on novel experimentation showing that users could in fact recognise paired stimulation accurately. Analysis of results of use of the paired/single dimension was found in psychophysical testing to significantly increase the information transmission capabilities of the device.

In a preferred form, the speech processor/stimulator unit includes filter means for enabling a stimulating current to represent high frequency components of the speech signal.

The stimulating currents are preferably applied to the first or second electrodes and one of the third to eighth electrodes when an unvoiced stimulus is required.

The novel modifications to the Speech Processor Strategy include the following:

incorporation of specific filters to provide a specific stimulus in relation to high frequency components in the speech signal;

use of a paired stimulus rather than a single stimulus to encode the presence of an unvoiced versus voiced speech component, or to encode F1 information in addition to F2;

implementation of this strategy to incorporate a paired stimulus being delivered to electrode 1 or 2, plus one of electrodes 3 through 8 in relation to an unvoiced stimulus.

BRIEF DESCRIPTION OF THE DRAWINGS

FIGS. 7 to 12 illustrate typical stimulator circuitry for the speech processor 2, in which.

DESCRIPTION OF THE PREFERRED EMBODIMENT

Figure 1:
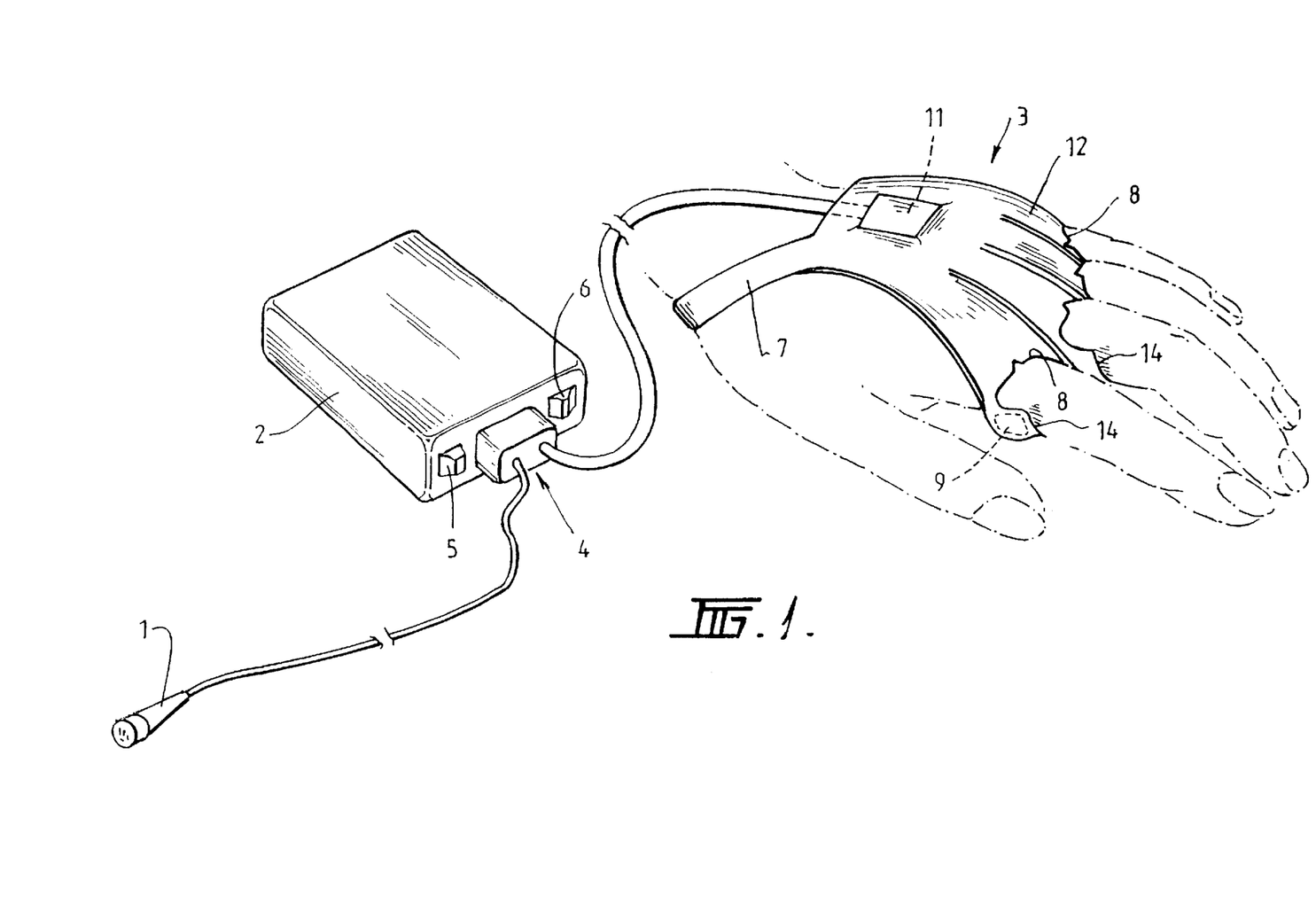
FIG. 1 shows the component parts of the electrotactile vocoder in use.

FIG. 1 shows the three main parts of the electrotactile vocoder embodying the invention: a microphone 1, a speech processor 2 and a handset 3.

The microphone 1 plugs into a socket 4 on top of the speech processor 2 and the speech processor has two controls, an on/off switch 5 and a sensitivity control 6. By turning up the sensitivity control it is possible to make the system more sensitive. When set on a higher sensitivity the speech processor 2 will pick up softer speech and environmental sounds around the user. The sensitivity control is not a volume control. The levels programmed into the speech processor during mapping act as the volume control for the system.

Figure 2:
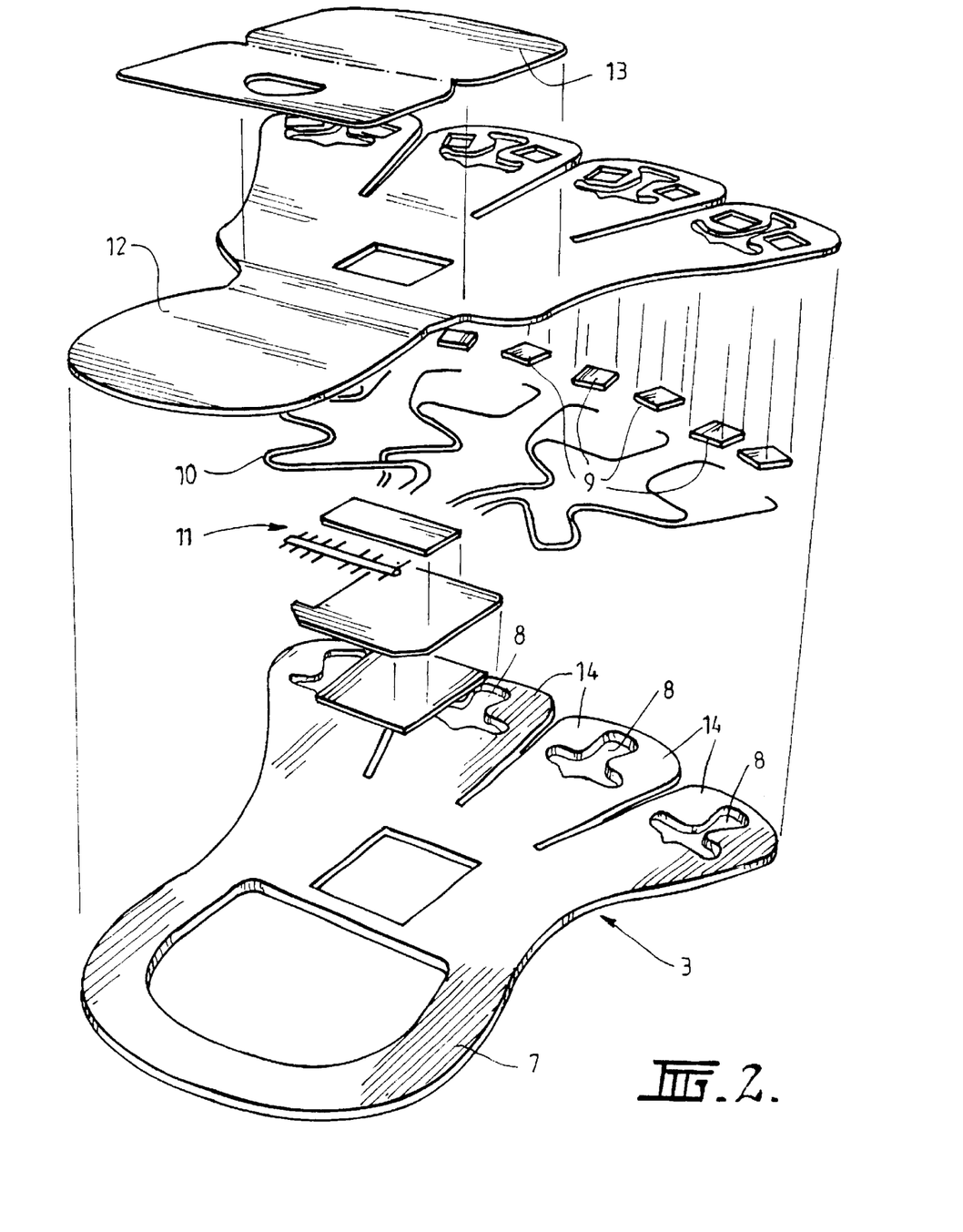
FIG. 2 is an exploded view of the handset for the electrotactile vocoder of FIG. 1.
Figure 3:
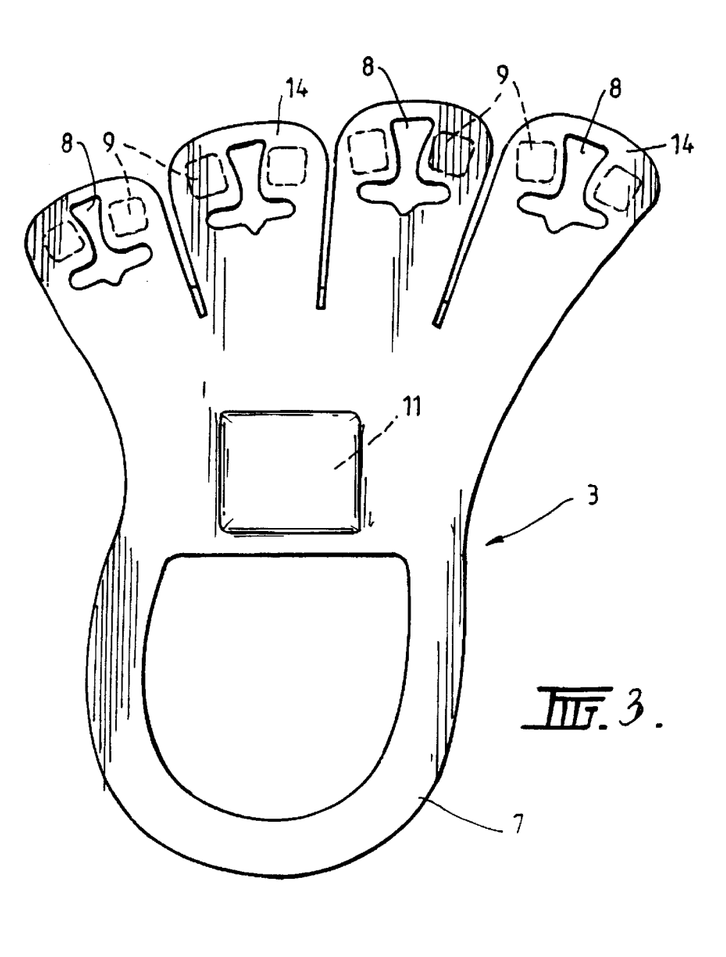
FIG. 3 is a top plan view of the handset showing the special configuration of the finger holes or rings.

As shown in FIG. 2, the flexible handset 3 is die cut from Neoprene or like resilient material and has a wrist strap 7 and four shaped rings or openings 8 for each of the four fingers of the hand. An electrode 9 is positioned on either side of each ring 8 to provide eight finger electrodes altogether. The electrodes 9 are electrically connected by wires 10 to a connector 11, the wires 10 and electrodes 9 being held in place on the handset 3 by an overlying layer 12 of polypropylene, such as Melco, adhesively secured to the handset 3 by a hot melt adhesive. The layer 12 includes a cover 13 which protects the connector 11 as shown in FIG. 3.

The rings 8 are defined by shaped openings in the handset 3 with each shaped opening including lobes 14 providing support for the electrodes 9. The lobes 14 are positioned at either side of the rings 8 to resiliently hold the electrodes 9 in contact with the sides of each finger when the handset 3 is fitted to the hand of a user.

Figure 4:
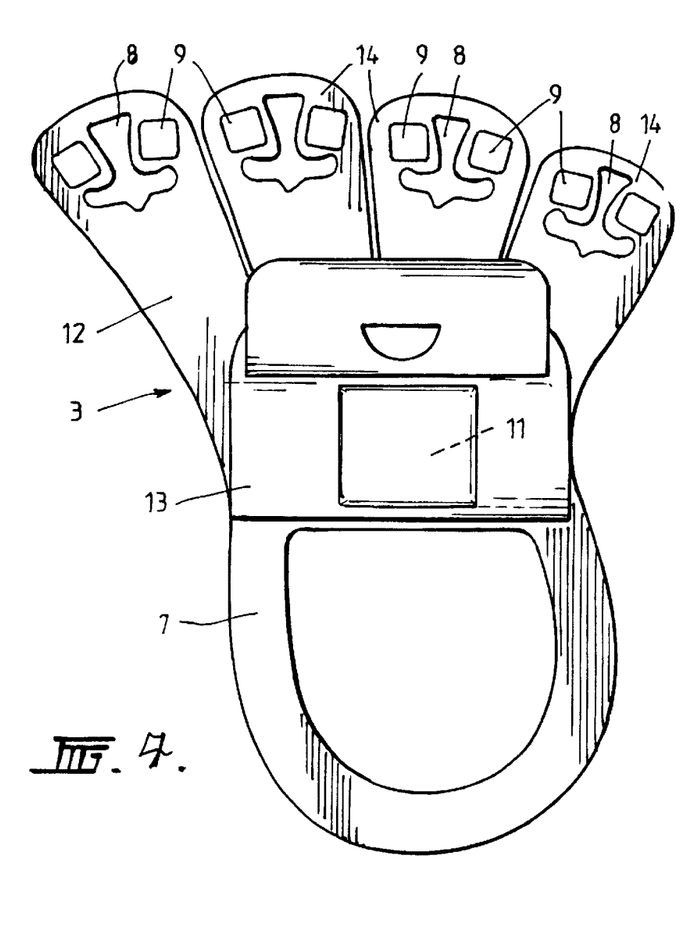
FIG. 4 is a bottom plan view of the handset with the flap raised to expose the electrical connector.
Figure 5:
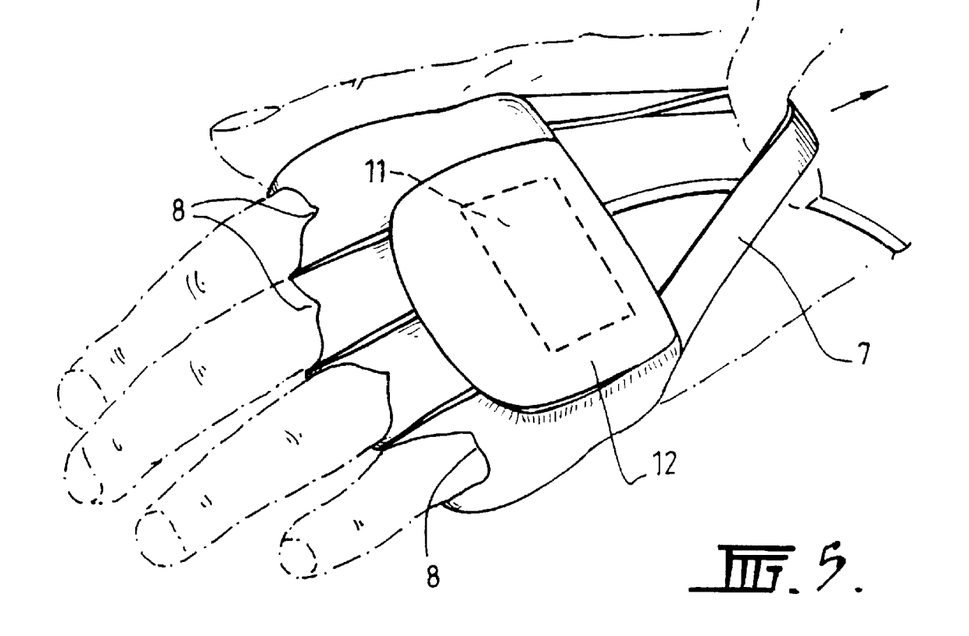
FIGS. 5 and 6 illustrate the fitting of the handset to the hand of the user.
Figure 6:
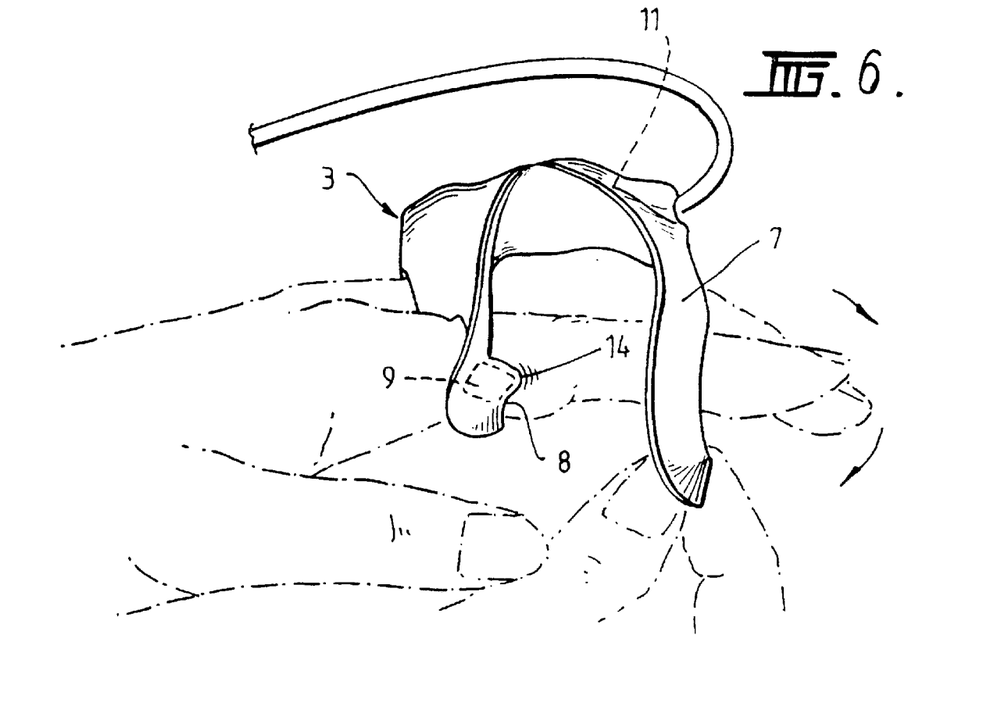

To put the handset on:
 (i) plug the small end of the handset cable into the row of pins under the flap on the underside of the handset;
 (ii) ease the cable connector into the square socket until it lies flat and close the flap and seal using the velcro dots;
 (iii) place the handset on the table with the electrodes facing up and the fingers pointing towards you (refer to FIG. 4);
 (iv) place the tips of the fingers of your left hand into the rings;
 (v) lift the handset up by the wrist strap and gently pull the handset onto the fingers;
 (vi) pull the wrist strap forward over the finger tips and put your hand through the wrist strap (refer to FIG. 5) and pull the wrist strap back around your wrist.

To take the handset off:
 (i) pull the wrist strap forward over the fingers and across the back of your hand;
 (ii) gently ease each ring part way down the fingers before removing them totally.

The handset cable 10 has a small connector 11 on one end, which plugs into the row of pins 12 under the flap on the underside of the handset (refer FIG. 3). The larger connector 13 at the other end of the cable plugs into the second socket 14 on top of the speech processor.

The Speech Processor Unit consists of four main functional parts:
 a wide-band directional microphone and associating cabling,
 a speech processor circuit,
 a stimulator circuit, and
 an interface for programming of the speech processor/stimulator.

These parts will be further described in relation to the preferred embodiment.
 (i) Input Microphone: The input microphone used is a directional, wide-band microphone, which allows input up to 7000Hz;
 (ii) Speech Processor Circuit: The speech processor receives information from the wide-band microphone. In the speech processor circuitry, specific features of the incoming waveform are detected, and measured, according to software directions provided to the circuitry through the speech processing strategy previously programmed. In the speech processor circuit, estimates of a number of speech features can be extracted. The outputs from the speech processor circuitry are then electrically encoded as a pulse width modulated signal according to the software directions contained within the speech processor encoder program, and the user's individual speech processor map (software which sets the threshold and comfortable stimulus pulse widths for each individual electrode). The speech processor circuit preferably incorporates a MSP speech processing board from Cochlear Limited. In addition, an alternative Digital Speech Processor Board version (using a Motorola 56000 processing chip) can be implemented.

The electrically coded speech information sent to the handset is based on those features of speech selected by the speech processor. Using the current UF2 speech processing strategy, the speech processor selects from the speech:
 1. an estimate of the fundamental frequency (F0) of the speech;
 2. an estimate of the second formant frequency (F2) of the speech;
 3. the amplitude of the speech; and
 4. an indication of the presence of high frequency information above 4 ktHz.
 5. an indication of the unvoiced/voiced speech feature for consonants.

These speech features are encoded differently by the speech processor (refer to Table 1). As a result of changes in the electrically encoded signal sent to the handset, changes in these features are perceived by the user as changes in the stimulation (refer to Table 1). F0 is electrically encoded as pulse rate. Changes in F0 are perceived by the user as changes in the "roughness" of the stimulation. F2 is electrically encoded as the electrode selected to be turned on, and is perceived by the user as the particular electrode providing stimulation. The amplitude of speech is encoded as pulse width. Changes in the pulse width of the stimulation is perceived by the user as changes in the intensity of stimulation. The presence of high frequency information, such as is produced by high frequency fricatives, is encoded to be presented to the user as stimulation on electrode 8.

The presence of an unvoiced consonant is encoded by activation of electrode 1, in addition to the F2 or high frequency electrode, and perceived by the user as a "paired stimulus".

Each speech feature presented is designed to help the user improve their understanding of speech. The perception of roughness (F0) provides information on syllable stress and consonant voicing. Use of this information would help the user to perceive syllable number and stress, vowel duration and consonant manner. The perception of which electrode is stimulating (F2) provides information on vowel formants and high frequency fricatives. This will enable the user to discriminate F2 and detect high frequency information.

TABLE 1

Summary of the speech features selected, their electrical coding, tactile signal and help in understanding speech.

| Speech Feature | Electrical Coding | Tactile Parameter | Information |
| --- | --- | --- | --- |
| F0 | pulse rate | roughness of stimulation | syllable number & stress vowel duration consonant manner |
| F2 | electrode turned on | electrode providing stimulation | vowel formant |
| speech waveform amplitude | pulse width | intensity of stimulation | intonation pattern of speech phoneme duration |
| high frequency information | electrode 8 | stimulation on electrode 8 | presence of high frequency fricative |

TABLE 1-continued

Summary of the speech features selected, their electrical coding, tactile signal and help in understanding speech.

| Speech Feature | Electrical Coding | Tactile Parameter | Information |
| --- | --- | --- | --- |
| voiced/unvoiced consonant | electrode 1 | stimulation on electrode 1 and F2 electrode | presence of an unvoiced consonant |

Using the software it is possible to implement alternative speech processing strategies in the speech processor. This inbuilt flexibility allows for future implementation of speech processing strategies tailored to provide specific information.

Referring to FIGS. 7 to 11, the stimulator circuitry decodes the pulse width modulated (pwm) signal from the processor and houses the circuitry to stimulate the relevant electrode. Novel features incorporated into the stimulator circuitry include:

- the method of implementing the stimulus without use of a separate ground or return electrode, and
- the method of electrically isolating the user from the electrical supply, ensuring patient safety.

Figure 7:
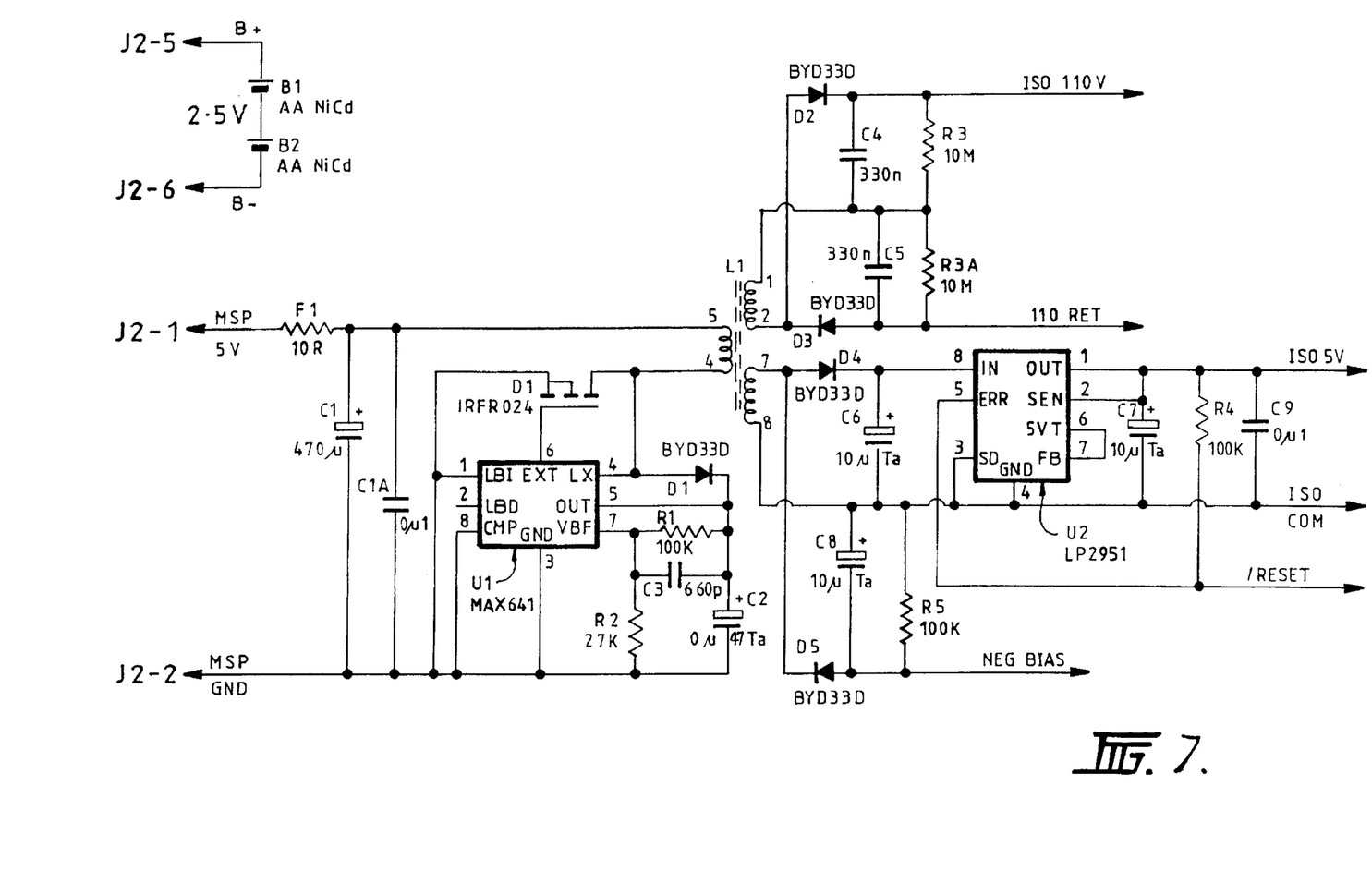
FIG. 7 shows the stimulator power supply.
Figure 8:
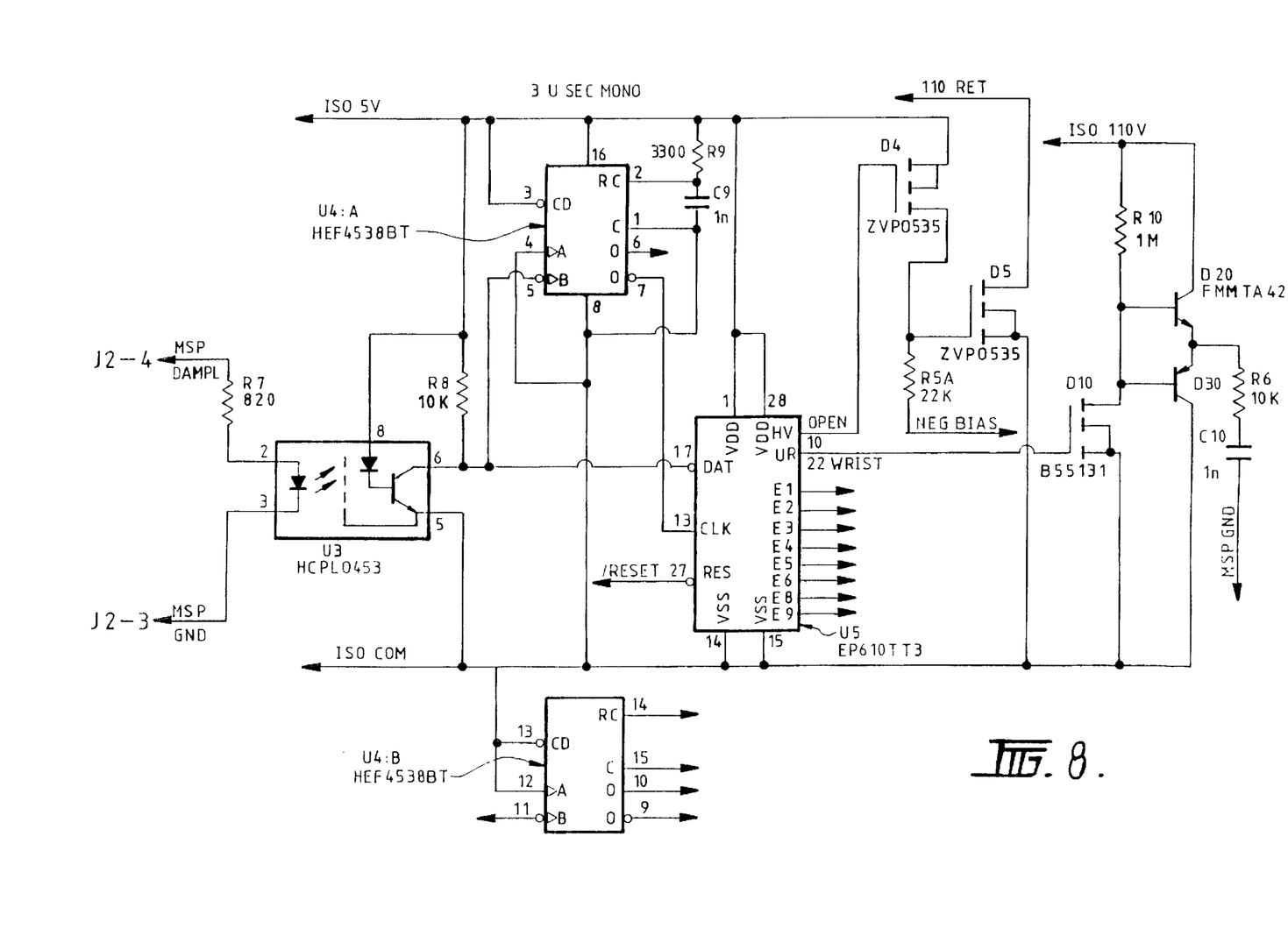
FIG. 8 shows the Stimulator logic circuit.
Figures 9, 10:
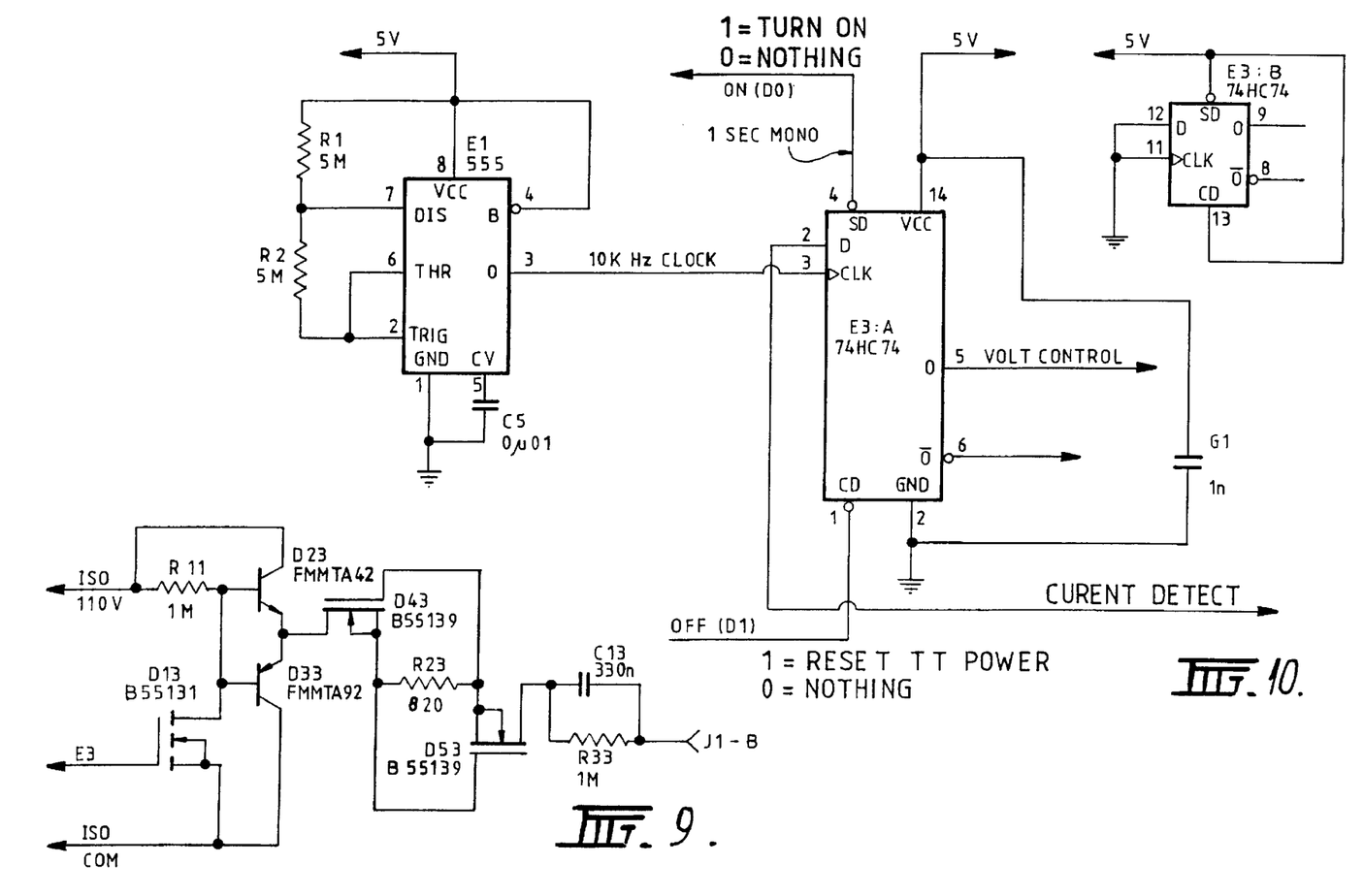
FIG. 9 illustrates a typical stimulator output circuit for each electrode.
FIGS. 10 to 12 show the interface circuitry for the stimulator.

Specific details of the circuitry allowing for electrical isolation include the following:

- Transformer L1 in FIG. 7, typically a Siemens EFD15 No 7 core, supplies isolated 5V for components and isolated 110V for the stimulation of the electrode.
- Capacitors C4 and C5, in FIG. 7, are used to generate the 110V for the stimulation.
- The pulse width modulated signal from the processor is passed through the optocoupler, U3 (FIG. 8). This provides isolation between the processor and the stimulator.
- U4 provides timing for clock used to shift data into the programmable chip U5 (FIG. 8).
- U5 is a programmable chip, which decodes the MSP Dampl(Data) signal into the relevant electrode. FIG. 8 illustrates the circuitry that are implemented in U5. The circuitry consists of a shift register which shifts the pwm signal into the binary to decimal decoder. The output of the decoder signifies which electrode is selected. The output of U5 is such that when one electrode is active all the other electrodes are inactive and the inactive electrodes operate as a common/ground. In this way, no wrist electrode, or other large common/ground electrode, is required as in the prior art.
- A time delay in the dampl signal is implemented by switching off the 110V isolated supply in the 110 return path. There is no current flowing during the 100us gap. The open signal from U5 controls the switching. Q4 in diagram 2 is OFF when the open signal goes HIGH.
- At the output, the two MOSFETs form a bipolar current regulator circuit. The capacitor in series with the 1M resistor prevents DC current from flowing.
- separate returns are used for the battery power source $B_1$, $B_2$ the MSP 5V supply and the opto-coupler U3 (FIG. 8).
- FIG. 8 illustrates a switching circuit 010,020,030 which connects the MSP to the common/ground of the inactive electrodes via capacitor C10 to reduce noise.

The interface is powered by two 9V alkaline batteries. These batteries also supply the power during programming. Power is not drawn from the computer.

The aim of mapping is to ensure that the device user always receives a stimulus that is above threshold and pleasant, yet strong enough to convey the maximum amount of speech information. The parameters used to specify the electrotactile stimulus are the threshold level (T-level) and comfortable level (C-level) pulse widths. The pulse width may be selected from the range 10 –1000 microseconds. A change in the pulse width of stimulation results in a change in the current being used to produce the stimulus. For the user this results in a change in the perceived strength of the stimulation. Sensitivity to the electrotactile stimulus varies between people and also between the fingers of one person. As such, it is important that the parameters of the electrotactile stimulation can be specified for each of the individual electrodes.

The T-level will be set at the point at which the wearer is first able to detect the tactile stimulus. The C-level will be set at the point at which the wearer reports the stimulus to be strong but comfortable to receive ongoing for 5 to 10 minutes. The T and C-levels will vary across electrodes and, even more so, between subjects. In particular, the levels on the outer edges of the first and fourth fingers have been found to be higher than on the other 6 electrodes (perhaps due to the thickness of the epithelium). After all of the levels are set it is important for the clinician to sweep across the eight electrodes to allow the wearer to balance the stimulus received on each electrode. The levels should be balanced so that when speech information is presented stimulation is balanced across the electrodes. Otherwise important information, such as loudness (perceived as strength of stimulation) may not be presented correctly, or weak stimulation may be masked by stimulation on adjacent electrodes.

It is necessary to set a threshold (T-level) and comfortable (C-level) for each electrode for each user. This can be quite an extensive process for the first map as the appropriate levels and the growth function of the sensitivity will vary greatly between different people and between the fingers of the same person. Subjects will not only need to learn the mapping process but become accustomed to the character of the stimulation. For this reason the clinician must be particularly careful when setting levels for the first map. Once the likely area of a level is identified, the mapping process is significantly simplified.

Most users will not find mapping an easy task during the first, and possibly subsequent sessions. The clinician must be careful to explain each step—particularly those requiring feedback from the user. As the feedback required is subjective, it is important that the clinician listens carefully and learns to make a judgement regarding the criteria the person is using to provide feedback. As the user has more experience regarding the concept of mapping the sensation provided by the device they will be more able to make accurate decisions regarding the level of stimulation. It is suitable during the first mapping session to encourage the user to report on the level of the sensation they are receiving without considering dynamic range or the actual appropriateness of the comfortable levels selected.

After new T and C-levels are set and balanced they need to be programmed into the speech processor. This is achieved by creating a "map". When a map is created it will use the most recent levels entered into the Measure Thresholds screen. Whenever the T or C-levels are changed a new map must be created. After the map is created it must be tested by the user. The act of testing a map writes that map into the memory of the speech processor. Any map that is written into the speech processor will remain in the processor until the next map is tested ie. written over the previous map. If testing indicated that the map was appropriate it can be saved on the user's disk for future use.

The frequency with which particular device users will require re-mapping will vary. It is important for mapping to occur weekly during the first two months, as levels will stabilise as the user becomes more familiar with the task and the stimulus. Regular checks will be required after this time, and should also be provided following any complaints by the user about the strength or quality of the stimulation.

PROGRAMMING AND PROGRAMMING INTERFACE

Figure 11:
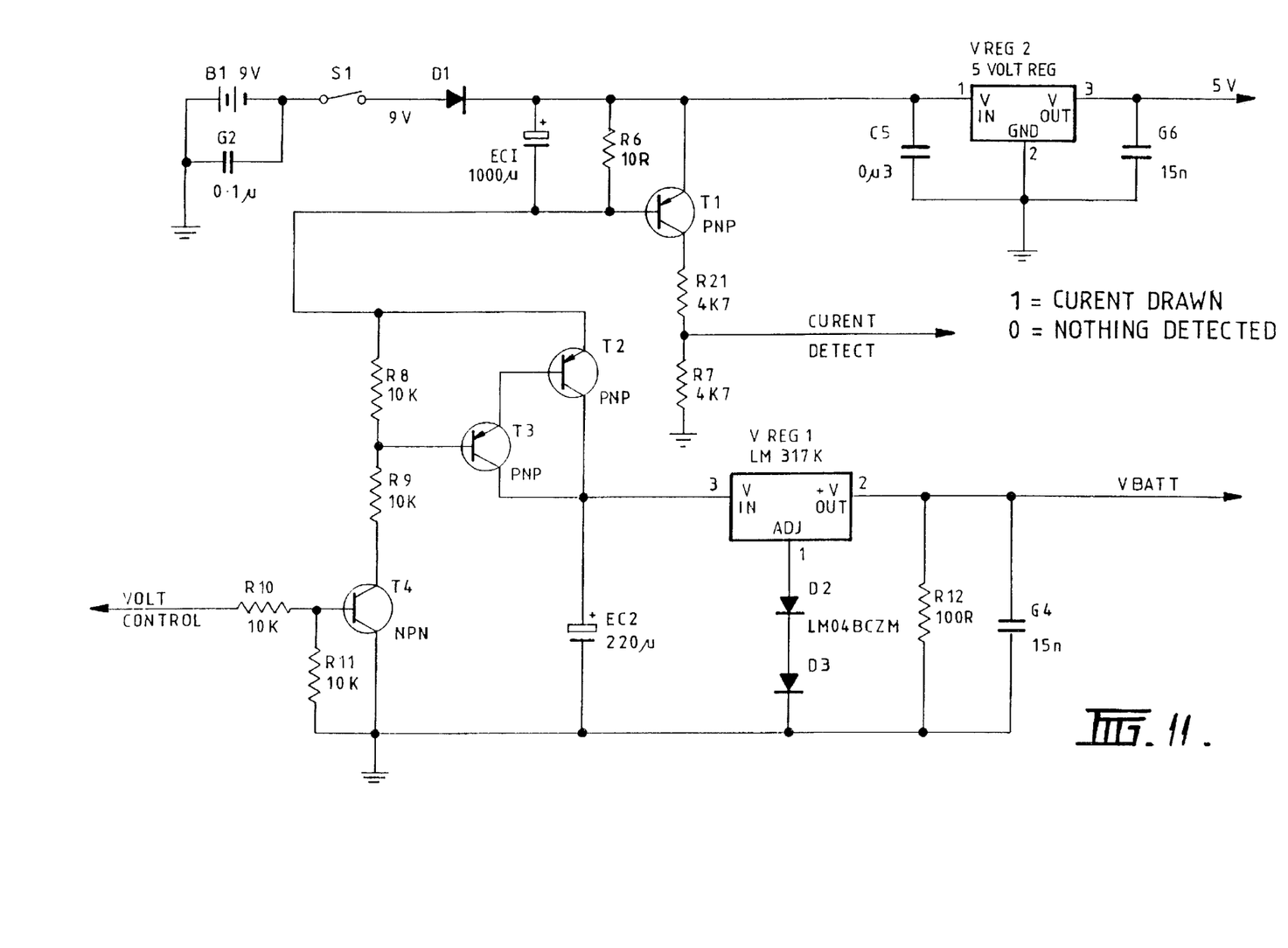
Figure 12:
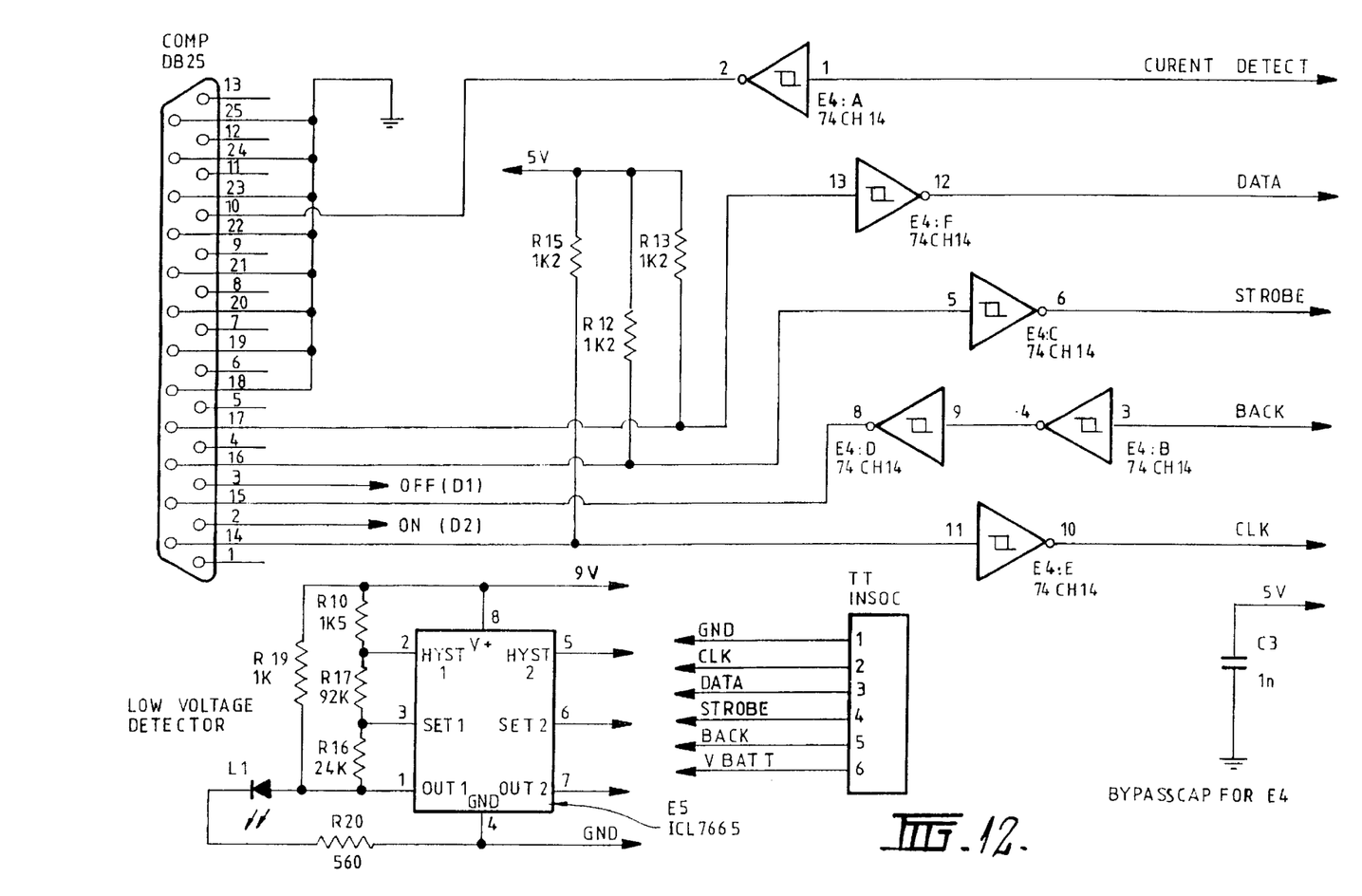

The programming interface is shown in FIGS. 11 and 12. It functions to allow commands from the computer software program to be passed to the Speech Processor Unit, allowing programming of encoder strategy and patient map. The Programming Interface has a dedicated power switch. Power is supplied for approximately 1 second when turned on via the software. The power will continue to be on if the connections are correct. If the connections between the speech processor and the computer are not complete the power will be switched off. This is to ensure that there will not be power when the programming system is not connected correctly or has come loose during use.

The interface system acts as the interface between the computer and the speech processor. The interface system consists of:

1. the computer cable
2. the programming interface
3. the speech processor cable The computer cable connects the computer to the programming interface. One end of the computer plugs into the parallel port of the computer (the port usually reserved for the printer), the other end plugs into the computer port on the programming interface. The speech processor cable plugs into the speech processor port on the programming interface and connects it to the speech processor.

The programming interface uses two PP3 9 volt batteries. These batteries also supply power to the speech processor whilst it is connected to the interface. The programming interface must be switched off when not in use to avoid draining the batteries. When the battery voltage is below 7 volts the programming interface may not reliably maintain the connection to the speech processor. At this voltage level the red "Low Voltage" light on the front panel of the programming interface will illuminate. This light will also be illuminated if the programming interface is connected to the computer but not turned on.

What is claimed is:

1. An electrode handset for an electrotactile vocoder, including a body, four finger members extending outwardingly from said body, each finger member having a shaped opening for receiving a finger and defining a ring-like member encircling the finger while leaving the fingers substantially free, opposed pairs of electrodes positioned adjacent each opening so as to make electrical contact with opposite sides of each finger in the region of the digital nerve when the fingers are inserted into the finger openings of the finger members, said ring-like members holding said electrodes in electrical contact with said fingers while allowing flexing of the hand or fingers without substantially affecting said electrical contact, said body also including an opening defining a wrist engaging strap for holding the handset on a hand with said electrodes engaging said fingers.

2. The handset of claim 1, wherein the body is made from a single piece of resilient material having an outlined shape defining said finger members, said shaped openings being cut from said finger members.

3. The handset of claim 1, wherein said each shaped opening has lobes positioned at either side of each shaped opening, said electrodes being positioned on said lobes so that the electrodes are presented and held in contact with the sides of the fingers in the region of the digital nerves when the fingers are inserted through the openings and the handset fully engages the hand.

4. An electrotactile vocoder including a handset carrying stimulating electrodes which are positioned by the handset when worn to be in electrical contact with the fingers to facilitate stimulation of the digital nerves of the user, a speech processor/stimulator unit for producing electrical stimulus at the electrodes based on incoming speech and other information, said stimulator unit including circuit means for applying stimulating current to said electrodes and for switching at least selected ones of said electrodes to a non-active state when stimulating current is applied to any one of the other electrodes, and means for utilising the electrodes in said non-active state as ground or return electrodes for said circuit means.

5. The vocoder of claim 4, wherein said circuit means includes means for sequentially applying stimulating currents to more than one electrode simultaneously.

6. The vocoder of claim 5, wherein said stimulating currents are applied to selected pairs of electrodes.

7. The vocoder of claim 4, wherein said circuit means includes programmable means which applies said stimulating current to selected electrode(s), said circuit means further including a shift register means for shifting a pulse width modulated signal into a binary to decimal decoder having an output which causes the circuit means to select the electrode(s), the output of said programmable means causing the selected electrode(s) to be active and all remaining electrodes to be inactive, said inactive electrodes acting as common or ground electrodes in the circuit means.

8. The vocoder of claim 4, wherein said circuit means further includes means to supply isolated voltage to said circuit means for stimulation of said electrode(s).

9. The vocoder of claim 8, wherein said means to supply isolated voltage includes optocoupler means for isolating the speech processor from the stimulator circuit means.

10. The vocoder of claim 8, wherein said means to supply isolated voltage includes means for switching the isolated voltage supply off during a time delay period in the stimulus current, and bipolar current regulator circuit means for preventing direct current flow to said electrode(s).

11. An electrotactile vocoder including a handset carrying stimulating electrodes which are positioned by the handset when worn to be in electrical contact with the fingers to facilitate stimulation of the digital nerves of the user, a speech processor/stimulator unit for producing electrical stimulus at the electrodes based on incoming speech and other information, said stimulator unit including circuit means for applying stimulating currents to said electrodes, said stimulator unit including means for encoding the presence of unvoiced speech components, or for encoding information relating to a first formant $F_1$ in addition to information relating to a second formant $F_2$, and for applying stimulating currents to selected electrodes.

12. The vocoder of claim 11 wherein said stimulating currents are applied sequentially to selected pairs of electrodes.

13. The vocoder of claim 11, wherein the speech processor/stimulator unit includes filter means for enabling a stimulating current to represent high frequency components of the speech signal.

14. The vocoder of claim 11, wherein said stimulating currents are applied to first or second electrodes and one of the third to eighth electrodes when an unvoiced stimulus is required.

* * * * *